(12) United States Patent
Del Medico

(10) Patent No.: US 6,902,567 B2
(45) Date of Patent: Jun. 7, 2005

(54) DEVICE FOR FIXING BONE SECTIONS SEPARATED BECAUSE OF A FRACTURE

(75) Inventor: Nilli Del Medico, Orbassano (IT)

(73) Assignee: Silvana Vese (IT)

( * ) Notice: Subject to any disclaimer, the term of this patent is extended or adjusted under 35 U.S.C. 154(b) by 0 days.

(21) Appl. No.: 10/296,741

(22) PCT Filed: May 28, 2001

(86) PCT No.: PCT/EP01/06090

§ 371 (c)(1),
(2), (4) Date: May 8, 2003

(87) PCT Pub. No.: WO01/91660

PCT Pub. Date: Dec. 6, 2001

(65) Prior Publication Data

US 2003/0171754 A1 Sep. 11, 2003

(30) Foreign Application Priority Data

May 31, 2000 (IT) ..................................... TO2000A0501
Sep. 27, 2000 (IT) ..................................... TO20000167 U

(51) Int. Cl.[7] ........................... A61B 17/56; F16B 39/02
(52) U.S. Cl. ........................... 606/71; 606/73; 411/271; 411/325; 411/60.2
(58) Field of Search .............................. 606/69, 72, 73, 606/70, 71; 411/271, 325, 55, 57.1, 60.1, 60.2

(56) References Cited

U.S. PATENT DOCUMENTS

| | | | | |
|---|---|---|---|---|
| 990,065 A | * | 4/1911 | Sargeant | 411/271 |
| 1,025,008 A | * | 4/1912 | Miner | 606/71 |
| 1,150,114 A | * | 8/1915 | Hays | 411/148 |
| 3,042,961 A | * | 7/1962 | Tieri | 16/228 |
| 3,547,114 A | * | 12/1970 | Haboush | 606/71 |
| 3,782,374 A | | 1/1974 | Fischer | |
| 4,388,921 A | * | 6/1983 | Sutter et al. | 606/71 |
| 4,438,762 A | | 3/1984 | Kyle | |
| 4,628,923 A | | 12/1986 | Medoff | |
| 4,988,350 A | | 1/1991 | Herzberg | |
| 5,360,452 A | * | 11/1994 | Engelhardt et al. | 623/22.37 |
| 5,904,683 A | * | 5/1999 | Pohndorf et al. | 606/61 |
| 6,282,999 B1 | * | 9/2001 | Hite et al. | 81/445 |
| 6,287,044 B1 | * | 9/2001 | Huber | 403/297 |
| 6,302,887 B1 | * | 10/2001 | Spranza et al. | 606/73 |
| 6,485,493 B1 | * | 11/2002 | Bremer | 606/70 |
| 6,533,789 B1 | * | 3/2003 | Hall et al. | 606/69 |
| 2003/0171753 A1 | * | 9/2003 | Collins et al. | 606/69 |

FOREIGN PATENT DOCUMENTS

| | | |
|---|---|---|
| EP | 0649635 | 4/1995 |
| FR | 782462 | 6/1935 |
| FR | 2686788 | 8/1993 |
| WO | WO 00/04836 | 2/2000 |

* cited by examiner

Primary Examiner—Pedro Philogene
Assistant Examiner—David A Bonderer
(74) Attorney, Agent, or Firm—Carlson, Gaskey & Olds

(57) ABSTRACT

A device (2) for fixing bone sections separated because of a fracture comprises a plate (4) with bores (8) for the fastening to a bone, a plurality of internally hollow barrels (10), screwed in the bores (8) of the plate (4) and a plurality of compression screws (6) adapted to be screwed in the bone and then locked in the barrels (10).

15 Claims, 8 Drawing Sheets

DEVICE FOR FIXING BONE SECTIONS SEPARATED BECAUSE OF A FRACTURE

BACKGROUND OF THE INVENTION

The present invention relates to a device for fixing bone sections separated because of a fracture.

More particularly, the invention relates to a plate and screw assembly for osteosynthesis, allowing immobilising one or more fractures in a long bone, such as a femur or a tibia.

Generally the plates have elongate shape ad are available in different models, depending on the shape and size of the bone they are to be applied to.

For instance, patent application WO 97/08999 discloses a plate for fixing fractures in the end section, or head, of a bone. Such a plate has an elongate portion that can be fastened to the bone through a plurality of screws, and an end portion including a barrel that is inserted into the bone to receive a compression screw. The compression screw is previously screwed into the bone; subsequently, after having located the plate with the barrel, the screw is fastened by a traction screw allowing compression of the plate against the bone.

Generally, compression screws are used in the bone head, whereas conventional screws of small size are used for fastening the plate to the bone shaft.

The barrel, which is integral with the plate, allows a rigid connection of the plate and the screw, thereby eliminating any clearance that might arise between the two parts.

Yet, the presence of the fixed barrel makes the plate application complex, since it is necessary to previously drill a bore in the bone, and hence use of special guides and tools is indispensable.

European patent EP 0 649 635 discloses a plate equipped, at its end portion, with two parallel barrels adapted to be inserted into the bone head. Also in this case the plate is fastened to the bone through a plurality of conventional screws, whereas compression screws are introduced in correspondence of the barrels. The presence of two barrels further increases the application difficulty, since two perfectly parallel suitably offset bores are to be drilled in the bone so as to allow a precise introduction of the barrels.

An alternative solution to using barrels is disclosed in PCT patent application WO 97/20313. That document discloses a special system for coupling a screw head and a corresponding opening in the plate. More particularly, the screw has an expansion head that, when expanding, becomes tightly locked in an opening of complementary shape in the plate. Yet such a solution, while allowing a certain rigidity in the screw-plate connection and making operations simpler, does not provide the same structural rigidity as the barrels.

SUMMARY OF THE INVENTION

It is an object of the invention to provide a plate for osteosynthesis, which is equipped with a plurality of barrels to be coupled with compression screw and which can be readily and safely applied.

The above and other objects are achieved by means of the device made in accordance with the invention, as claimed in the appended claims.

The plate made in accordance with the invention can be manufactured in different shapes and sizes to suit to different bone shapes and, thanks to the modularity of the barrels, can be used for different fracture types. Moreover, thanks to the provision of removable, and hence interchangeable, barrels, the plate can match screws of different lets and sizes.

BRIEF DESCRIPTION OF THE DRAWINGS

The above and other objects of the invention will become more readily apparent from the following description of a preferred embodiment, with reference to the accompanying drawings, in which.

DETAILED DESCRIPTION OF THE PREFERRED EMBODIMENT

Figure 1:
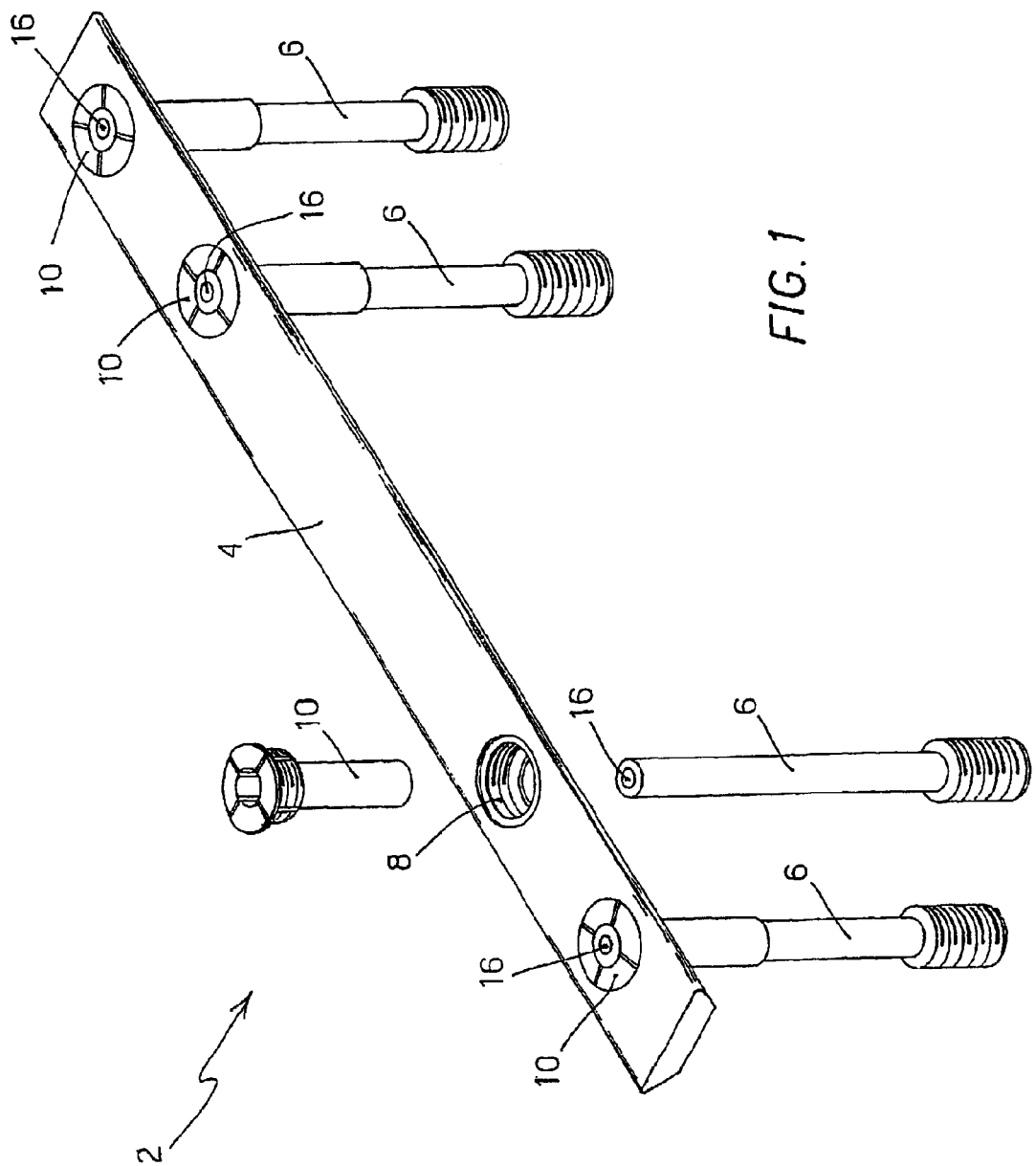
FIG. 1 is a perspective view of an osteosynthesis device made in accordance with the invention.

Referring to FIG. 1, a device 2 for fixing bone sections separated because of a fracture comprises a plate 4 with four threaded bores 8, four barrels 10 and four compression screws 6.

Barrels 10 are separate from plate 4 and therefore are interchangeable at will; they may have different lengths and internal diameters, depending on the requirements and on the bone type. The illustrated embodiment shows four identical barrels, and is suitable for fractures in the shaft of bones like femur or tibia.

Figure 2:
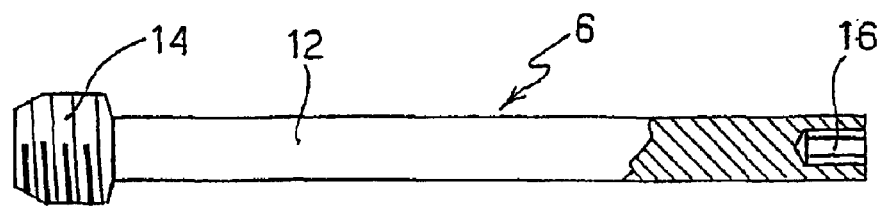
FIG. 2 is a partial cross sectional view of a compression screw used in a device made in accordance with the invention.

Each compression screw 6, shown in detail in FIG. 2, has no widened head and comprises an elongate body, with an external diameter corresponding with the internal diameter of barrel 10, a threaded end 14 insertable into the bone, and a hexagonal hollow 16 allowing screwing screw 6 in the bone by means of a suitable screw-driver tool, not shown.

Figure 3:
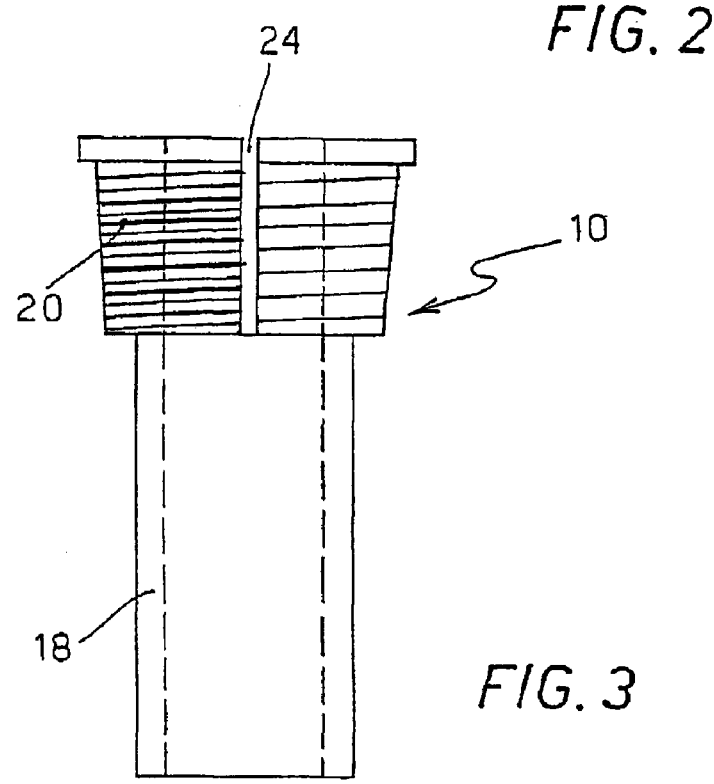
FIGS. 3 and 4 are a side and a top view, respectively, of a barrel used in a device made in accordance with the invention.
Figure 4:
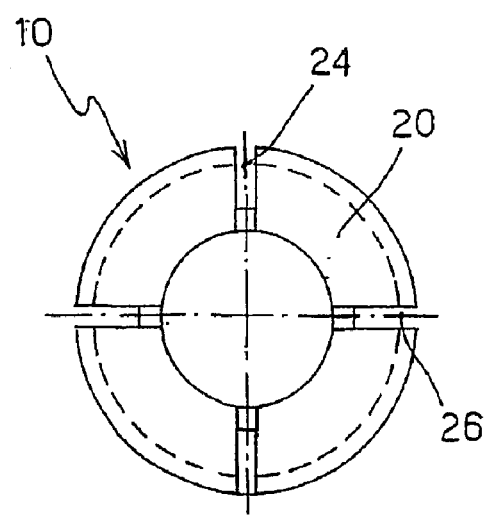

Barrels 10 are instead shown in detail in FIGS. 3 and 4. Each barrel 10 has an elongate and internally hollow cylindrical portion 18, projecting from plate 4 in order to penetrate into the bone, and an externally threaded frustoconical end portion 20. End portion 20 has two mutually perpendicular slots 24, 26, passing through the barrel axis. Such slots allow barrel end portion 20 to be radially compressed while the barrel is being screwed in plate 4, thereby gripping elongate body 12 of the corresponding compression screw 6.

Barrels 10 are screwed in plate 4, after screws 6 have been inserted into the bone, through a suitable tool, not shown in the drawings, which e.g. engages slots 24 and 26. To prevent the simultaneous rotation of screws 6 while the barrels are being screwed, it is possible to simultaneously use the same tool as previously used for screwing the screws, now in order to prevent their rotation.

Figure 5:
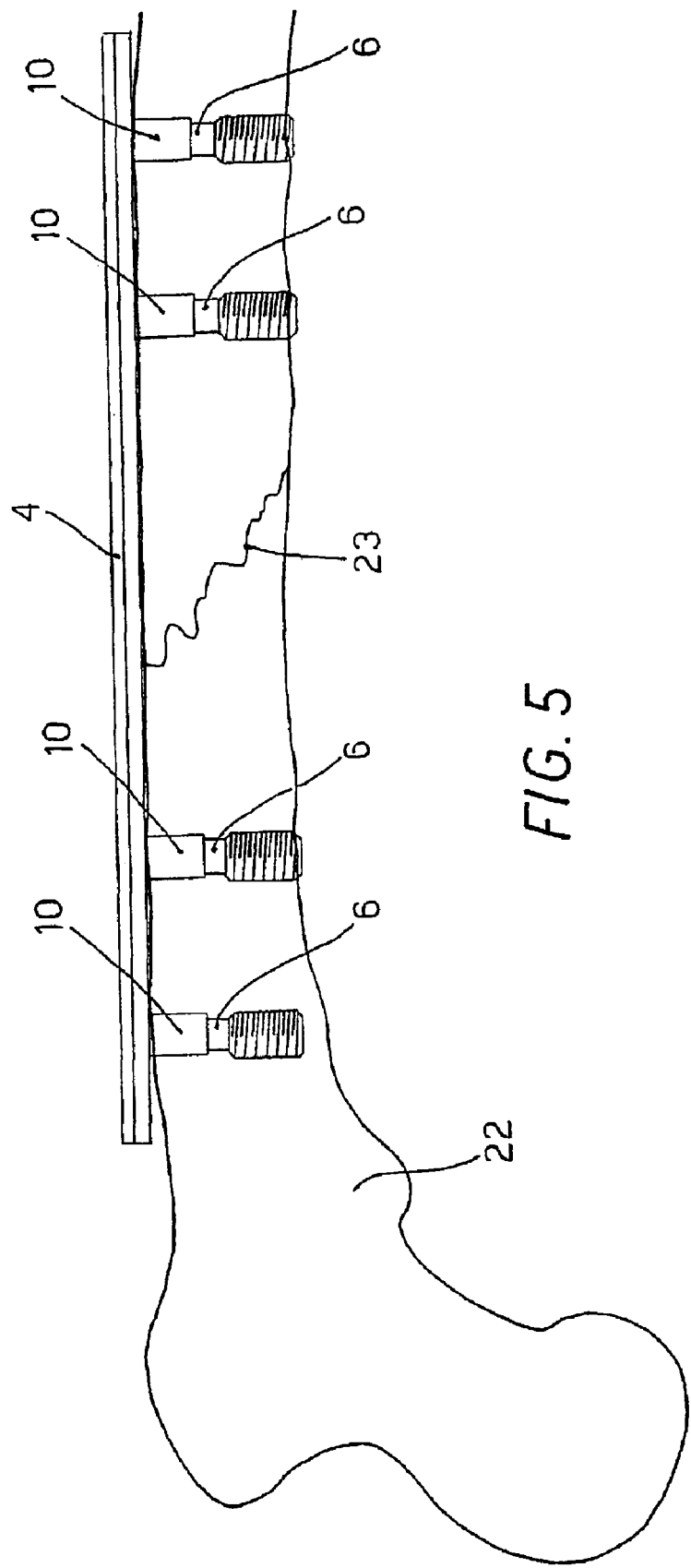
FIG. 5 is a schematic side view of an osteosynthesis device made in accordance with the invention, when applied to a femur.

FIG. 5 shows the device shown in FIG. 1 when applied to a femur 22 where a fracture line 23 is present. Screw 6 and barrels 10 are inserted into the bone, whereas plate 4 remains outside the bone and ensures the structural rigidity of the system. The length of each barrel 10 and each screw 6 may be chosen at will, to suit the bone type and the position, depending on the requirements.

The possibility of separating barrels 10 from the corresponding plate 4 makes the application of the above described device to the fractured bone considerably simpler.

The application is carried out by the following steps:

plate 4 is laid on the bone with barrels 10 already screwed, but in reverse position, i.e. projecting away from the bone;

the bores for compression screws 6 are drilled by using the barrels as guides;

plate 4 is removed and the bores are partly widened for the subsequent barrel insertion;

compression screws 6 are screwed in the bone;

the plate without the barrels is positioned;

barrels 10 are screwed and automatically grip the elongate bodies of screws 6 thereby locking the screws into position.

Figure 6:
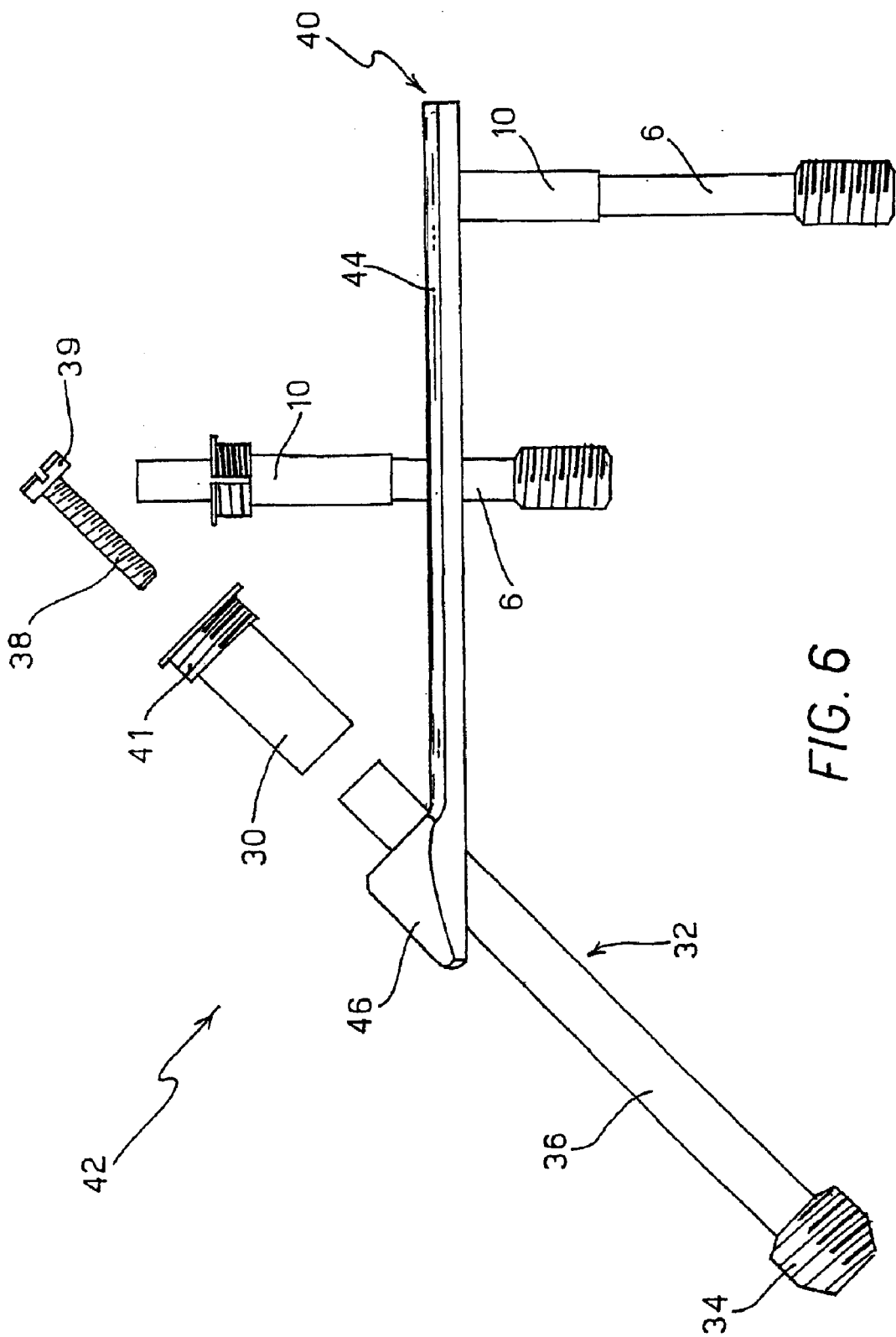
FIG. 6 is a side view of a variant embodiment of an osteosynthesis device made in accordance with the invention.

FIG. 6 shows instead a variant embodiment of a device 42 for fixing bone sections, made in accordance with the present invention. In particular device 42, which has been designed for fixing a fracture in a femur head, comprises a plate 40 having an elongate portion 44, into which two barrels 10 of the kind previously described and shown in FIGS. 3 and 4 are introduced, and an inclined end portion 46, adapted to house a different kind of barrel 30.

Barrel 30, that has a greater size than the other barrels 10, has a cylindrical threaded end portion 41 where the two slots typical of barrels 10 are not provided. Indeed barrel 30 is screwed in a corresponding threaded bore in plate 40, but it is not used to grip the body of the corresponding compression screw 32. Indeed compression screw 32, having an elongate body 36 and a threaded end 34, also includes a separate head 38, 39 that is screwed in a corresponding bore provided in body 36 of the screw itself. Head 38, 39 is actually a screw, having a threaded body 38 and a widened portion 39, which screw is introduced and abuts into a cavity in barrel 30, so as not to project from the plate.

Barrel 30 and compression screw 32 allow attaining a stronger compression of the bone sections, whereas barrels 10 allow using headless compression screws.

Figure 7:
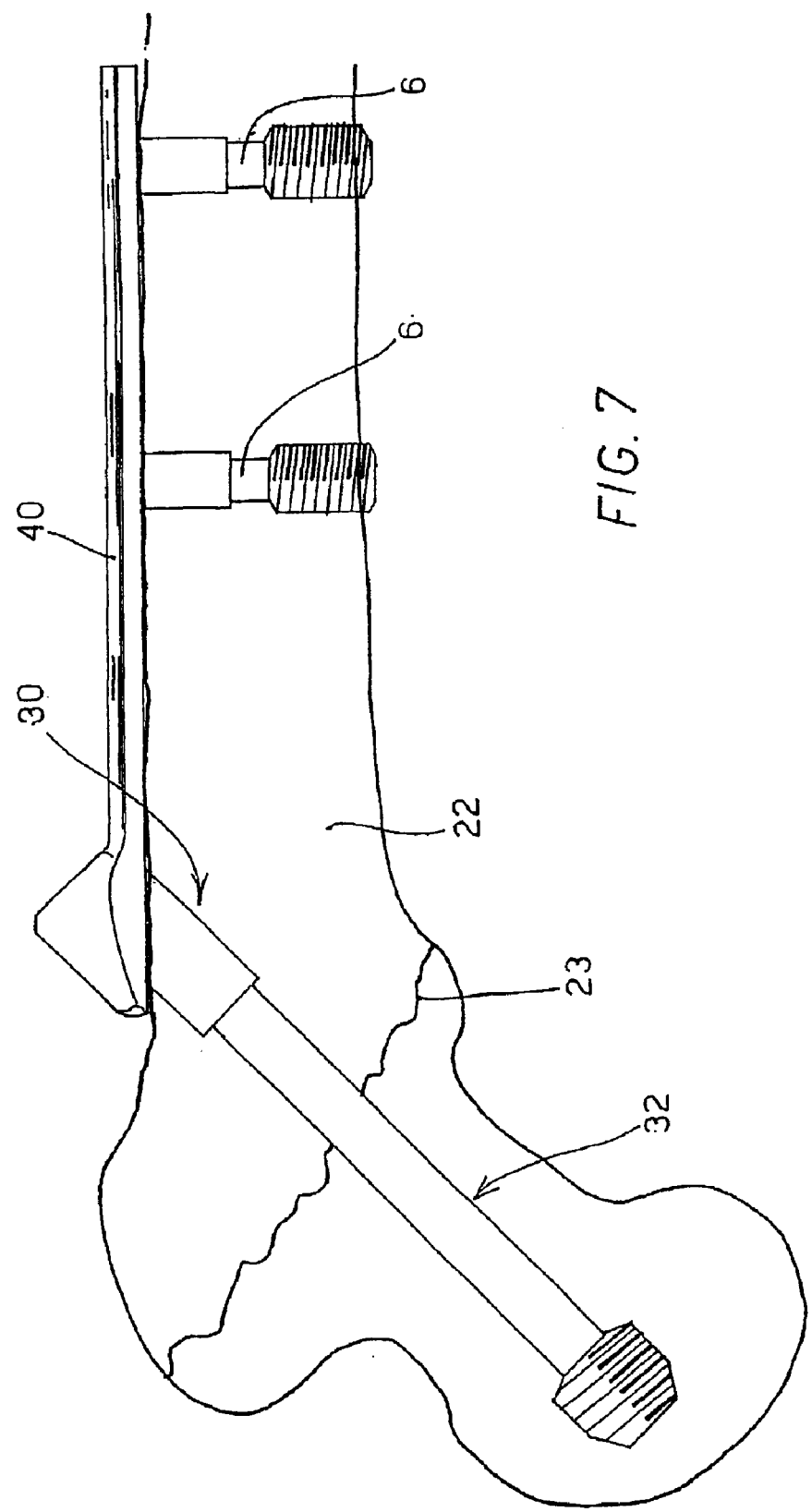
FIG. 7 is a side view of the device shown in FIG. 6, when applied to a femur.

FIG. 7 shows the device of FIG. 6 when applied to a femur 22. Screws 6 fasten plate 40 to the bone shaft, and screw 32 compresses the two bone sections separated by fracture line 23.

Figure 8:
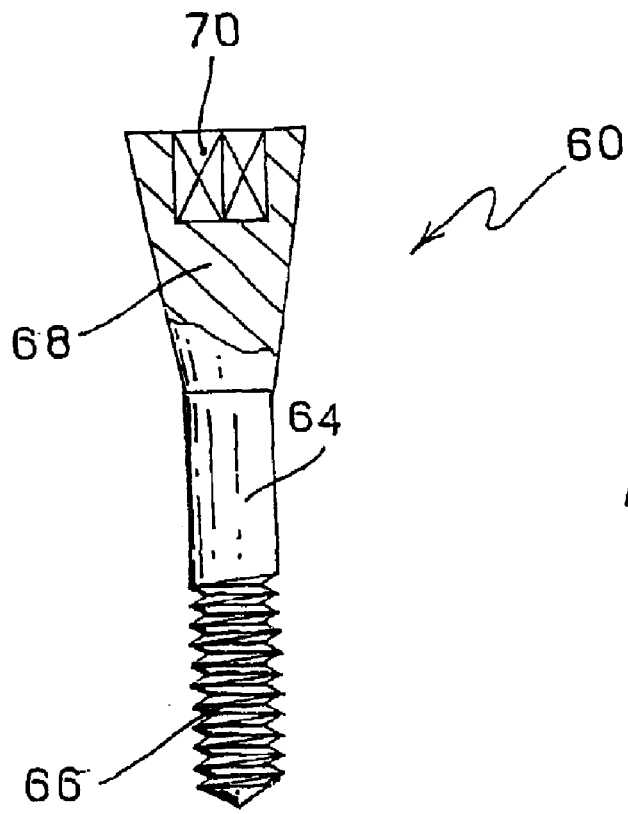
FIG. 8 is a front view, partly in cross section, of a compression screw made in accordance with a second exemplary embodiment of the present invention.
Figure 9:
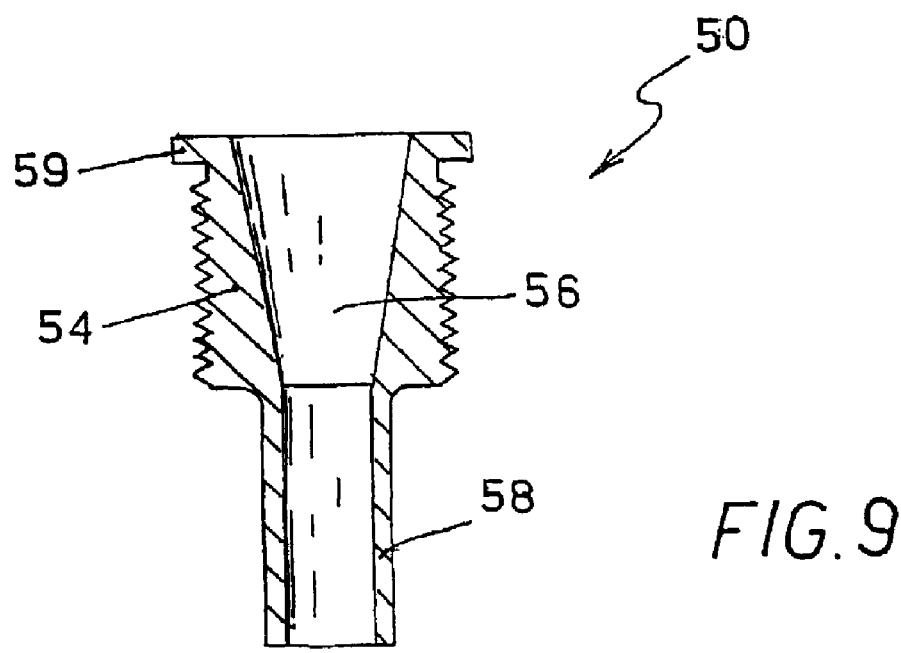
FIG. 9 is a cross sectional view of a barrel that can be coupled with the screw shown in FIG. 8.

FIGS. 8 and 9 show a second exemplary embodiment of a screw-barrel pair made in accordance with the present invention.

Screw 60, shown in detail in FIG. 8, comprises an elongate body 64 having at one end a threaded portion 66 adapted to penetrate into the bone, and at the other end a frustoconical head 68. Head 68 also has, in its upper part, a hexagonal cavity 70 intended to receive a screw-driving tool.

The characteristics of threaded portion 66 and the screw size, for instance the length and the diameter of the screw, may vary depending on the kind of fracture and of bone.

FIG. 9 shows instead in detail barrel 50 into which screw 60 is inserted for being screwed in the bone. Barrel 50 has an externally threaded cylindrical first portion 54 defined upwardly by an abutment ring 59, and an elongate cylindrical portion 58. The latter projects from the plate onto which the barrel is screwed and penetrates into the bone thus guiding screw 60.

Through-hole 56 inside barrel 50 has constant cross-sectional size within elongate cylindrical portion 58, whereas it has a frustoconical and outwardly open shape within the cylindrical first portion 54, so as to perfectly match the body and the head of screw 60.

Actually screw 60, when being screwed in the bone, is locked inside barrel 50 thereby eliminating any clearance that may arise between the two parts.

Figure 10:
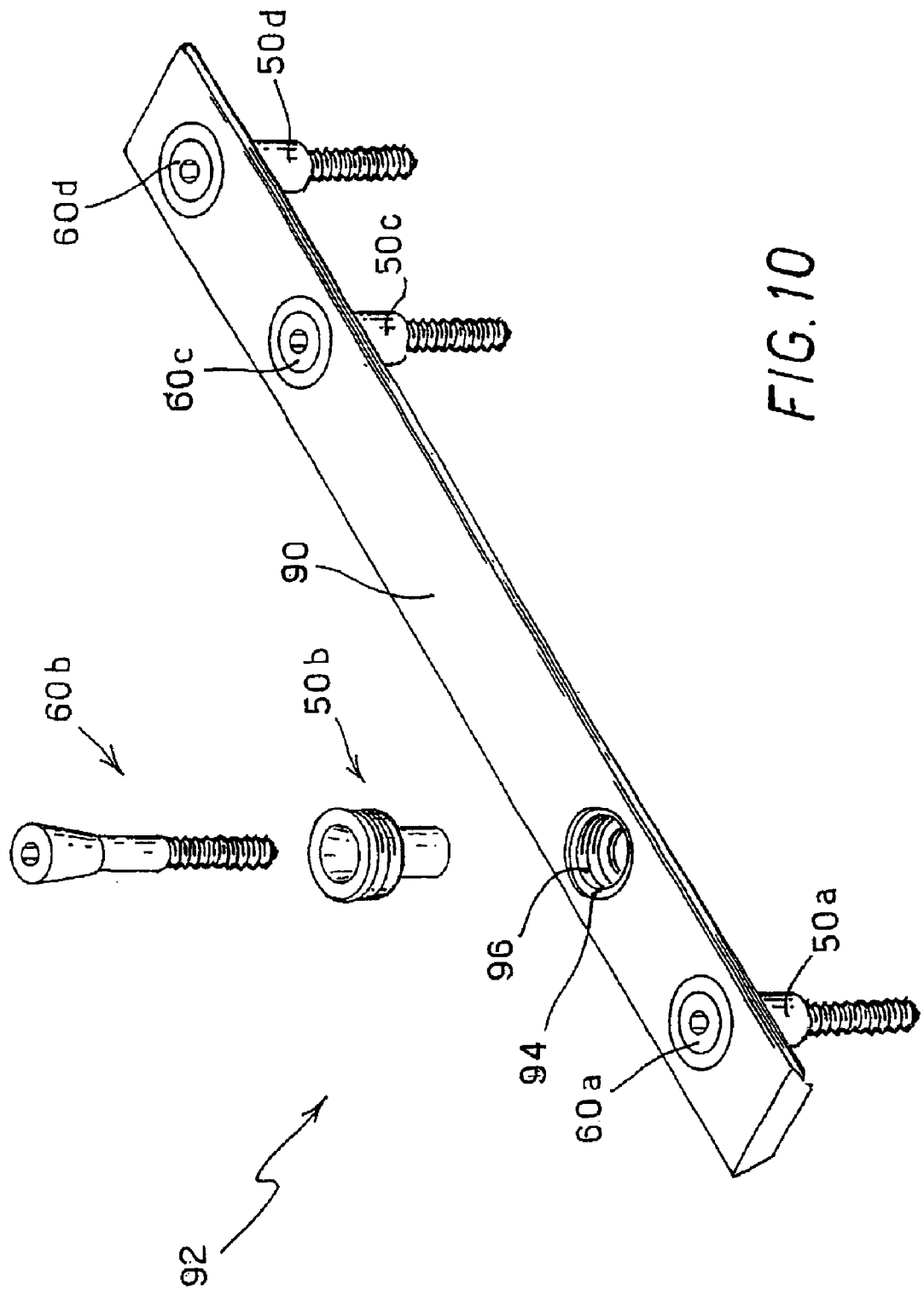
FIG. 10 is a perspective view of a plate including a plurality of barrels and screws made in accordance to FIGS. 8 and 9.

Barrel 50 may be coupled with an osteosynthesis plate like that shown in FIG. 10, which shows a further variant embodiment of a device 92 for fixing bone sections made in accordance with the present invention. Osteosynthesis plate 90, which can be coupled with several barrels 50, has four seats 96 with a cylindrical internal thread, adapted to house four corresponding barrels 50a–50d. Four screws 60a–60d are then used to fasten plate 90 to the bone.

When a barrel 50 is screwed into a corresponding threaded bore 96 in the plate, as shown in FIG. 10, abutment ring 59 is received into a corresponding ring cavity 94 formed in the plate about threaded bore 96, so that there is no projecting portion.

Figure 11:
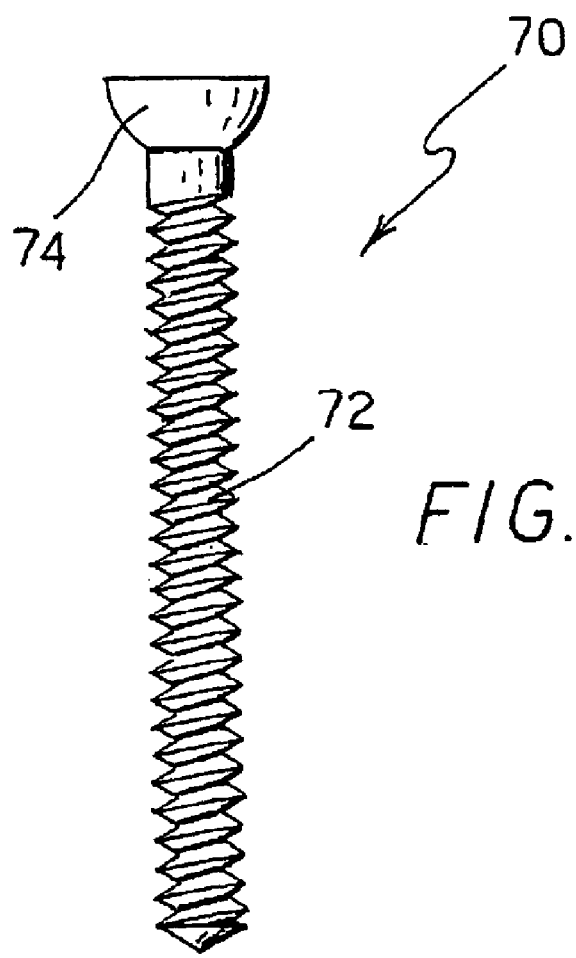
FIG. 11 is a front view of a compression screw made in accordance with a third exemplary embodiment of the present invention.
Figure 12:
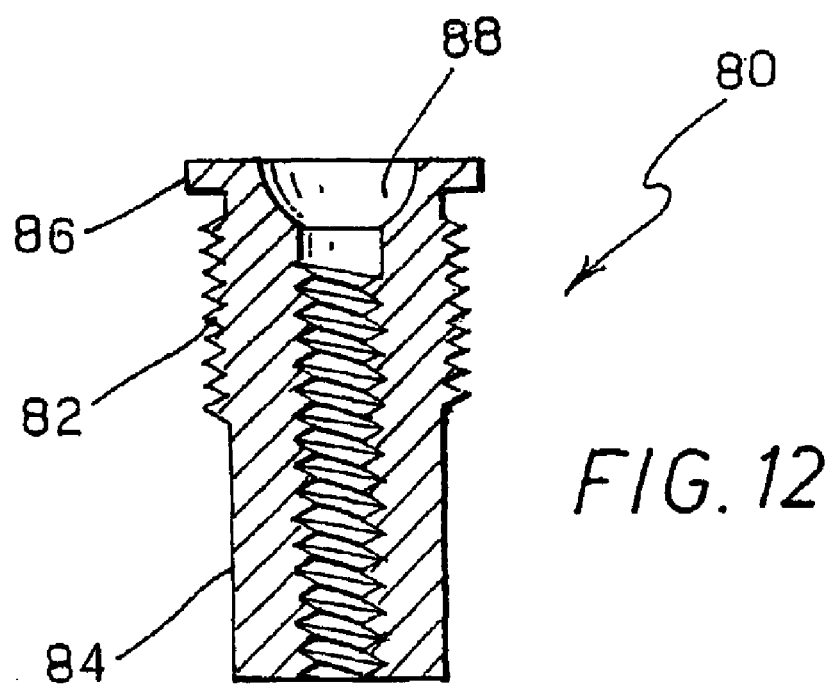
FIG. 12 is a cross sectional view of a barrel that can be coupled with the screw shown in FIG. 11 and the plate shown in FIG. 10.

FIGS. 11 and 12 show a third exemplary embodiment of a screw-barrel pair, made in accordance with the present invention, which may be coupled with a plate of the type shown in FIG. 10, i. e. a plate having internally threaded cylindrical seats 96.

Screw 70, shown in detail in FIG. 11, comprises a threaded elongate body 72 and a head 74 equipped, in its upper portion, with an hexagonal hollow, not shown in the drawing, adapted to receive a screw-driver tool. The kind of thread and the size of screw 70, e.g. its length and diameter, may vary depending on the fracture and the bone kinds.

FIG. 12 shows instead in detail barrel 80 into which screw 70 is received for being then screwed in the bone. Barrel 80 has an externally threaded cylindrical first portion 82 upwardly defined by an abutment ring 86, and an elongate cylindrical portion 84. The latter projects from the plate onto which the barrel is screwed and penetrates into the bone thus guiding screw 70.

The through-hole inside barrel 80 is internally threaded and has in its upper portion a seat 88 adapted to house head 74 of screw 70. The internal thread assists in the penetration of screw 70 into the bone, during the application, and at the same time it allows locking the screw within the barrel when the screw itself is completely screwed.

Interchangeability of the screw-barrel pairs with respect to the plate being used allows choosing the plate kind independently of the kind of screw/barrel used, depending on the requirements and the bone kind. Plate 90 shown in FIG. 10 is suitable for instance for fractures in the shaft of bones like femur or tibia.

The application of plate 90 by means of the screw devices previously disclosed with reference to FIGS. 8, 9 and 11, 12 is carried out by the following operations:

plate 90 is laid on the bone for drilling the four bores where screws 60 or 70 will be subsequently screwed;

plate 90 is removed and the bores are somewhat widened for the subsequent insertion of the projecting portions of barrels 50 or 80;

barrels 50, 80 are screwed in plate 90 and the latter is positioned on the bone, thereby making the projecting portions of the barrels penetrate into the corresponding bores;

screws 60, 70 are screwed in the bone and, when becoming locked within the barrels, they fasten plate 90 to the bone.

Interchangeability of the barrels allows anyway obtaining a high flexibility of employ, since it is possible to choose each time the most suitable screw kind, and the corresponding barrel, by using thus a conventional plate.

Another example of an osteosynthesis implant assembly is disclosed in FR 2686788 which refers to a modifiable combination of a series of support plates shaped for fixing to the shaft of the femur by means of screws. A series of coupling sleeves of different lengths and angular position are also provided, capable of being secured to the top end of the plate by means of conical coupling between the sleeves and the bores in the plate. FR 782462 discloses a device for osteosynthesis of the type comprising a plate to be mounted outside the injured leg and to be fixed by means of screws, which comprises a series of sleeves screwed in the plate.

What is claimed is:

1. A device for fixing bone sections separated because of a fracture, the device comprising;

a plate with a plurality of bores for fastening said plate to said bone by means of screws thus allowing compression of the plate against the bone;

at least one barrel internally equipped with an axial through-hole, said barrel being located in correspondence with one of said bores, said bore being a threaded bore and said at least one barrel and said plate being separate pieces that can be rigidly coupled by screwing said barrel in said threaded bore;

at least one compression screw adapted to be received in said barrel and screwed in said bone; wherein said at least one barrel has an elongate portion projecting from said plate and a threaded end portion adapted to be screwed in a corresponding threaded bore in said plate.

2. A device according to claim 1, wherein said barrel has an elongate cylindrical portion adapted to penetrate into said bone, and a threaded frustoconical end portion where two mutually perpendicular slots pass through the barrel axis are formed, which slots allow said end portion to become radially compressed during screwing of the barrel into the plate.

3. A device according to claim 2, wherein said end portion of the barrel, during screwing of the barrel in the plate, grips the end portion of said compression screw, thereby locking it within the barrel.

4. The device according to claim 1, comprising a plurality of threaded bores each adapted to receive a barrel for locking a corresponding compression screw.

5. The device according to claim 1, wherein said elongate portion of said barrel is cylindrical and is adapted to penetrate into said bone.

6. A device for fixing bone sections separated because of a fracture, the device comprising:

a plate with a plurality of bores for fastening said plate to said bone by means of screws thus allowing compression of the plate against the bone;

at least one barrel internally equipped with an axial through-hole, said barrel being located in correspondence with one of said bones;

at least one compression screw adapted to be received in said barrel and screwed in said bone, said bore where said barrel is located is a threaded bore and said at least one barrel and said plate are separate pieces that can be rigidly coupled by screwing said barrel in said threaded bore wherein said barrel has an elongate cylindrical portion adapted to penetrate into said bone, and a threaded end portion adapted to be screwed in a corresponding threaded bore in said plate.

7. A device according to claim 6, wherein said barrel has a longitudinal internal cavity into which a compression screw is inserted, said compression screw comprising an elongate body with a threaded end, which is partly introduced into said cavity, and a head which is screwed, at the side opposite to said barrel, in said elongate body to lock said compression screw in said barrel.

8. A device according to claim 7, wherein said head is a screw including a threaded portion, which is screwed in the elongate body of said compression screw, and a widened end portion, which abuts against the barrel thereby allowing compressing the plate against the bone.

9. A device according to claim 6, wherein said through-hole of said barrel has a frustoconical, outwardly open first portion, and said screw has a frustoconical head, of complementary shape to the frustoconical first portion of the hole of the barrel, so that, when said screw is inserted into the barrel and screwed in the bone, the head is locked by compression within the corresponding frustoconical portion of the barrel.

10. A device according to claim 9, wherein said elongate cylindrical portion of the barrel has smaller external diameter than said threaded first portion.

11. A device according to claim 6, wherein said through-hole of said barrel is internally threaded to engage a threaded elongate body of the compression screw.

12. A device according to claim 6, wherein said cylindrical first portion of the barrel is defined upwardly by an abutment ring that, when the barrel is screwed in the plate, is received in a corresponding annular cavity formed about the bore receiving said barrel.

13. A device for fixing bone sections separated because of a fracture, the device comprising;

a plate with at least one threaded bore for fastening said plate to the bone;

a barrel having a threaded end portion adapted to be threaded into said at least one threaded bore for securing said barrel to said plate, and a cylindrical portion adapted to penetrate the bone; and a threaded member adapted to be received within said barrel and screwed into said bone.

14. The device as recited in claim 13 wherein said barrel includes an axial threaded bore for receiving said threaded member.

15. The device as recited in claim 14 wherein said threaded member comprises a compression screw.

* * * * *